United States Patent
Brockman (10) Patent No.: US 7,695,489 B2
(45) Date of Patent: Apr. 13, 2010

(54) DEVICES AND RELATED METHODS FOR TARGETED PRESSURE AND TEMPERATURE THERAPIES FOR PELVIC REGION DISORDERS AND SYNDROMES

(75) Inventor: Iliana Chea Brockman, Tampa, FL (US)

(73) Assignee: IC Relief, LLC, Tampa, FL (US)

( * ) Notice: Subject to any disclaimer, the term of this patent is extended or adjusted under 35 U.S.C. 154(b) by 959 days.

(21) Appl. No.: 11/475,996

(22) Filed: Jun. 28, 2006

(65) Prior Publication Data

US 2007/0083238 A1  Apr. 12, 2007

Related U.S. Application Data

(60) Provisional application No. 60/694,792, filed on Jun. 28, 2005.

(51) Int. Cl.
*A61M 29/00* (2006.01)
*A61F 7/12* (2006.01)

(52) U.S. Cl. .......................... 606/197; 606/191; 607/1; 607/104; 607/105; 607/113; 607/114; 482/91; 482/121

(58) Field of Classification Search .................... 607/1, 607/104, 105, 113, 114; 606/191, 197; 600/29, 600/30; 482/91, 121

See application file for complete search history.

(56) References Cited

U.S. PATENT DOCUMENTS 3,939,842 A * 2/1976 Harris ........................ 607/113
4,696,302 A * 9/1987 Clark et al. .................. 607/113
2003/0149337 A1* 8/2003 Ritchie et al. ................. 600/38
2008/0281345 A1* 11/2008 Wise .......................... 606/191

OTHER PUBLICATIONS

Weiss, Jermone M. "Pelvic Floor Myofascial Trigger Points: Manual Therapy for Interstitial Cystitis and the Urgency-Frequency Syndrome." Dec. 2201. The Journal of Urology. vol. 166, 2226-2231.*
Weiss, Jerome M. "The Role of Myofascial Trigger Points in Interstitial Cystitus." Oct. 20, 1999.*

* cited by examiner

*Primary Examiner*—Roy D Gibson
*Assistant Examiner*—Kaitlyn E Helling
(74) *Attorney, Agent, or Firm*—Hogan & Hartson LLP (57) ABSTRACT

Disclosed herein are devices and related methods for using those devices in the relieving and/or treating of pain, discomfort, and/or inflammation in the pelvic region using targeted pressure and temperature delivery. The devices and methods for using those devices to deliver targeted pressure and temperature therapy internally to patients through their rectal or vaginal cavities are disclosed.

31 Claims, 3 Drawing Sheets

DEVICES AND RELATED METHODS FOR TARGETED PRESSURE AND TEMPERATURE THERAPIES FOR PELVIC REGION DISORDERS AND SYNDROMES

CROSS-REFERENCE TO RELATED APPLICATIONS

The present application claims the benefit of U.S. provisional patent application Ser. No. 60/694,792, filed Jun. 28, 2005.

BACKGROUND OF THE INVENTION

1. Field of the Invention

The present invention relates, in general, to devices and related methods for using those devices in the relieving and/or treating of pain, discomfort, and/or inflammation in the pelvic region using targeted pressure and temperature delivery. More particularly, the present invention relates to devices and methods for using those devices to deliver targeted pressure and temperature therapy internally to patients within their rectal or vaginal cavities.

2. Relevant Background

Many people suffer from pelvic floor dysfunction, painful bladder syndrome, vulvodynia and other non-infectious pelvic syndromes that cause them to experience pain or discomfort with intercourse, urination, defecation, or other physical activities. In some cases, pain and discomfort symptoms can occur sporadically or chronically without the particular suffering person being readily able to identify activities as potential causes for the symptoms. There is much speculation and research in the medical community that such non-infectious pelvic syndromes may be at least partially caused by muscles in the pelvic area (and the "pelvic floor" muscles in particular) that are too tight, strained or cramping. This is believed to cause these muscles to spasm or even to bear upon or pinch sensitive nerve bundles in the pelvic area, causing combinations of localized, generalized and referred pain and discomfort sensations.

In situations where strengthening or relaxing of the pelvic floor muscles or drug therapy does not resolve the patient's pelvic issues over time, surgical approaches are sometimes tried. For example, U.S. Pat. No. 6,862,480 describes a surgery entailing implanting a device for treating pelvic disorder that comprises an electronic implant, which includes a sensor, a microchip, and electrostimulator. The implant is adapted to sense muscle spasms and apply electrical stimulation through one or more electrodes to treat the disorder. As appropriate, the control unit may configure the current applied by the electrodes so as to treat various pelvic dysfunction related disorders, such as stress incontinence, fecal incontinence, interstitial cystitis, urine retention, or other sources of pelvic pain or discomfort. The use of the implant described in this patent, however, requires the patient to undergo a painful surgery, thus limiting its attractiveness and use significantly.

In situations where more traditional physical therapy or drug therapies do not resolve the patient's pelvic condition or disorder, there is a desire for medical providers to have exhausted all conservative treatment approaches before invasive therapies, such as surgery described in U.S. Pat. No. 6,862,480, are tried. In this regard, there is much recent research regarding so-called "trigger-points" and "tender points" for the cause of pain and discomfort. Myofascial tissue (also called "fascia") wraps around muscle tissue, muscle fibers, bundles of fibers, and the muscles themselves, and then continues on to form tendons and ligaments. When muscular dysfunction is present, muscles contract, or cramp, to varying degrees, which is known as "going into spasm." Ordinary muscle cramps and contractions release with movement, that is, stretching of the affected musculature. When the muscle is locked into a deep and painful spasm, it is said to form a "trigger point" or "tender point." These points do not release with stretching. Instead, they are locked into a strong state of contraction. This contraction is essentially a localized hardening of the muscle tissue and associated fascia.

To the touch, trigger and tender points feel like hardened knots in the otherwise softer surrounding tissue. Trigger points and tender points are generally distinguished from one another semantically in that they are classified as trigger points if they "refer" pain or discomfort sensations to other parts of the body or alternatively as tender points if they only cause localized pain or discomfort. Trigger points located in the pelvic floor muscles, due to the various nerve bundles located in that region, can cause referred pain to the bladder, urethra, vagina, vulva, testicles, rectum, and other areas of the pelvic region. When a muscle develops a trigger point (e.g., goes into spasm), it can compress or pinch different nerves, thereby sending messages of pain or other discomfort to the brain. Since nerves can pass through many muscles, sometimes the pain is "felt" in a muscle other than the originating site, causing a referred pain situation. Trigger points in particular are now widely speculated to cause referred pain for a variety of medical conditions, disorders, and syndromes causing or otherwise associated with pelvic pain, discomfort, or dysfunction.

As appreciation of the trigger point theory of pain and discomfort grows, many medical professionals are beginning to prescribe physical therapy sessions to treat or resolve trigger and tender points, in addition to or instead of drug and surgical therapies, as part of a regimen for treating various non-infectious pelvic syndromes and symptoms of pain, discomfort, or inflammation in the pelvic region. Myofascial trigger point therapy is one such physical therapy technique. It involves the systematic application of pressure to tender muscles and myofascial tissue in order to relieve pain, discomfort, and other symptoms of dysfunction with the goal of returning the muscles and fascia to their normal, relaxed states.

Myofascial trigger point therapy is a massage-type physical therapy technique that releases "trigger points" in the muscles in the pelvis or other areas. Trigger point therapy is the application of sustained, direct pressure onto a trigger point. In practice, this direct pressure is often repeatedly applied, and at different angles, to an identified trigger point. One theory regarding the mechanism of action is that the applied pressure interrupts various neural signals that cause one or more of the spasm and/or the pain. In any event, such pressure has been found to ultimately lengthen the muscle into its normal state and break spasm-pain-spasm cycles that cause referred and/or localized pain. It also enables the myofascial tissue to release any constriction, and return to its normal state, preventing further spasms.

In the particular case of utilizing myofascial trigger point therapy for the treatment of pelvic region syndromes and disorders, it is the case that many of the suspect pelvic floor muscles are most directly or most easily accessed internally. Given the difficulty of accessing internal trigger points in the pelvic floor muscles, the patients are often referred by their health care provider to a physical therapist that is specially trained to do internal myofascial trigger point release therapy. Oftentimes, such therapists will require the patient to perform exercises or follow-up therapies at home. Problems arise, however, when a particular patient does not have available a partner to assist in the home therapy. Anatomical limitations prevent such patients from being able to manually access the trigger points at home without an appropriately adapted treatment tool. Conventionally available tools, however, are not well suited for such purposes.

Many conventional physical therapy devices suitable for home use by a patient and designed for the pelvic region are particularly designed for general strengthening of the pelvic floor muscles (such as for incontinence or constipation), and not for providing targeted internal therapy such as trigger point therapy. For example, the performance of exercises to strengthen and/or retrain the pelvic floor muscles (e.g., Kegel exercises) can be augmented with various commercially available intra-vaginal and/or intra-anal devices adapted to facilitate or improve the performance of the pelvic exercises. Such intra-vaginal and/or intra-anal devices have included weighted apparatus such as intra-vaginal cones. Patients are instructed to insert the weighted and tapered cone into the vagina or rectum and squeeze their pelvic muscles in order to retain the device for a certain length of time. Other types of prior art devices include electromyographic (EMG) transducers or sensors which are insertable into or placed just outside of the vagina and/or anus to obtain EMG data indicative of baseline pelvic floor muscle tone and/or contraction(s) of the pelvic floor muscles during the performance of specific muscle contraction exercises. Such EMG data may be usable for diagnostic purposes as well as for monitoring the performance and/or effect of muscle training exercises. Thus, such conventional devices available on the market designed for home use in pelvic floor physical therapy are unsuitable for internal pelvic trigger point therapy.

Furthermore, it is conventional in many areas of medicine to use temperature therapies, including hot (thermal) and cold (cryogenic) packs or baths, to battle symptoms of pain and discomfort. Heat and cold can be used alternatively and are often used as a prelude to exercise or physical therapy.

Heat therapy in particular is known to induce vasodilation and assist in drawing blood into the target tissues. The increased blood flow delivers needed oxygen and nutrients, and removes cell wastes. Heat is also known to decrease muscle spasms, relax tense muscles, relieve pain, and increase range of motion. There are available many devices and mechanisms to provide thermal therapy, including a variety of commercial hot packs, hot water bottles, hot towels/compresses, electrical moist heat devices, disposable self-heating patches, hot baths and hydrocollators. These conventional devices and mechanisms, however, are directed to provide generalized heat therapy by application to the skin, making them largely ineffective in the targeted therapy of the pelvic region with thermal therapy.

Conversely, cold therapy produces vasoconstriction, which slows circulation and reduces inflammation, muscle spasm, and pain. Cryogenic therapy devices are available in many forms including a variety of commercial cold packs, ice cubes, iced towels/compresses, and forms of hydrotherapy. Like with conventional thermal therapy devices and mechanisms, conventional cryogenic therapy devices and mechanisms are not suitable for providing targeted temperature therapy in the pelvic region.

There are several devices that are commercially available for providing cryotherapy at and just inside the anus for hemorrhoid relief. For example, U.S. Pat. No. 5,800,485 describes a system that uses a finger-shaped projection for insertion into the rectum. The projection is cooled by a cold fluid (such as cold water) that circulates through channels within the projection, thus providing generalized cooling to the surrounding tissue. The system uses an electrical pump to circulate the cooling fluid. The projection used in this system is relatively short and has substantially the same diameter over its length due to its function of treating swelling around the anal opening. The design of the projection thus make this system incapable of reaching deeply into the vaginal or rectal cavities of the patient and manipulated to deliver targeted pressure or temperature therapy at particular treatment points. Further, the system of this patent is fairly complicated, requiring the user to provide a cooling fluid and power (batteries or an electrical outlet) for the pump.

Similarly, the cryotherapy device marketed under the trade name "Hemor~Rite" by FAMA Holdings International Corp. of Coral Springs, Fla., is adapted for applying cold therapy directly to the swollen hemorrhoidal veins to provide temporary relief of itching, pain, and swelling. The device comprises a traffic-cone shaped device that is filled with a ice-pack material that can be frozen in the freezer. The cone shaped device, once frozen, is directed for insertion into the rectum to deliver cold therapy generally in and around the area of the anus. The device is similar in shape to vaginal cones used for pelvic muscle exercising, having a substantial taper with its base being substantially larger in diameter than the distal end that pushes into the cavity. This shape makes the Hemo~Rite device incapable of reaching deeply into the vaginal or rectal cavities of the patient to deliver targeted pressure or temperature therapy.

Thus, there remains a need for improved devices and related methods for using those devices in the relieving and/or treating of pain, discomfort, and/or inflammation in the pelvic region using targeted pressure and temperature therapy.

SUMMARY OF THE INVENTION

It is an object of some aspects of the present invention to provide improved devices and methods for relieving pelvic pain, discomfort, inflammation, and other symptoms associated with pelvic region syndromes, disorders, conditions and diseases.

Also, it is an object of certain aspects of the present invention to provide novel treatment devices and methods for using those devices that can be easily and efficiently self administered by a person experiencing symptoms in the pelvic region, including pain or discomfort, at the time that the pain or discomfort is being experienced, thus obviating the need to schedule a treatment appointment with a therapist.

Also, it is also an object of certain aspects of the present invention to provide a novel device that is composed of material that enhances safety and sterility of the device, operates easily and effectively for providing targeted temperature therapy to internal tissues, and operates safety to reduce the risk of injuries due to misuse during self-administration of therapy.

The present invention provides devices and related methods for treating with targeted pressure and temperature therapy inflammatory and non-infectious vaginal, vulvar, anal and/or pelvic pain syndromes, and symptoms associated with or resulting from one or more vaginal or rectal diseases, conditions, disorders, or conditions.

The methods according to the present invention treat such syndromes and symptoms by using devices according to one or more embodiments of the present invention to provide one or more of targeted thermal temperature therapy, targeted cryogenic temperature therapy, and target pressure therapy internally via the vaginal or rectal cavities to one or more treatment sites within the pelvic region.

For example, according to embodiments of the present invention, one may reduce inflammation in the pelvic region by using devices according to embodiments of the invention to provide targeted cryogenic (i.e., cold) therapy via the vaginal cavity. Similarly, for example, according to other embodiments of the present invention, one may relax muscles by using devices according to embodiments of the invention to provide targeted thermal (i.e., heat) therapy via treatment points located within the rectum. Additionally, for example, devices according to embodiments of the present invention may be utilized to provide targeted pressure therapy, such as trigger point release therapy, internally to the pelvic region via the vaginal or anal cavities in conjunction with simultaneous targeted temperature therapy.

Such inflammatory and non-infectious pain syndromes can include pelvic floor dysfunction (entailing muscles of the pelvic floor, i.e., the area surrounding the rectum, vagina/scrota, and urethra, not contracting and/or relaxing properly), tension of the pelvic floor muscles (e.g., spasms of the pelvic floor muscles leading to recurring pelvic pain), painful intercourse or dyspareunia, internal pelvic floor trigger points or tender points, vaginismus (spasming of the muscles at the opening of the vagina), myofascial pain syndrome (referred pain from trigger points in the pelvic area), general vulvodynia, interstitial cystitis (a syndrome that may include suprapubic pain present in the lower abdomen, perineal pain present between the vagina and anus in women or the scrotum and anus in men, pain during sexual intercourse, and painful ejaculation), or chronic pelvic pain (including pressure or heaviness deep within the pelvis independent of or associated with intercourse, bowel movements, or sitting). Further, such inflammatory and non-infectious pain syndromes can result from or be related to medical physical therapy (e.g., patients may tense prior to therapy expecting discomfort or experience inflammation after vaginal or rectal therapy), or sexual activity (e.g., injuries resulting from sexual assault, or general tenderness, soreness and swelling resulting from consensual activities). Most preferably, the syndromes include pelvic floor dysfunction and interstitial cystitis.

Such symptoms associated with or resulting from one or more vaginal or anal/rectal diseases, conditions, or disorders include vaginal or rectal irritation, muscle tightness, burning, inflammation, pain, pressure, muscle spasms, circulation problems, and soreness. Preferably, such symptoms can be associated with or resulting from vaginal and/or anal/rectal diseases, conditions, syndromes and disorders including sexuality complications following cancer treatment (sexual side effects of cancer treatment can make resuming sex more difficult, especially for women being treated for breast or gynecological cancers that cause side effects that make sex painful or difficult), side effects and complications relating to bladder instillations (patients may tense prior to the instillation expecting discomfort, or experience irritation, burning, inflammation and possible flare-up of frequency, pressure and urgency post instillation), sexual complications associated with multiple sclerosis (e.g., nerve impulses interruption), irritable bowel syndrome, vaginal atrophy (such as results from decreases in levels of the female hormone estrogen), non-bacterial prostatitis (inflammation of the prostate can be accompanied by pelvic, groin or low back pain or urination complications), prostatodynia (e.g., pain in the genital area, pain with urination, or difficulty urinating), and proctitis (e.g., inflammation of the lining of the rectum called the rectal mucosa as side effect of medical treatments like radiation therapy or antibiotics). Additional vaginal and anal diseases, conditions, syndromes, and disorders the symptoms of which can be addressed according to the present invention include complications from vaginal or rectal exams (patients may tense prior to exam expecting pain or discomfort, or may experience irritation and inflammation after the exam), postpartum vaginal soreness (such as following resumption of sexual intercourse) and pain, vaginal and anal exercise and dilation (such as for the treatment of vaginismus and related disorders, and pre-natal perineal message), coccydynia (e.g., inflammation of the tailbone), proctalgia fugax, levator ani syndrome, anorectal pain, anissmus (including anorectal dysfunction that can contribute to constipation marked by the failure of pelvic floor muscles to relax, or a paradoxical contraction of the pelvic floor muscles with defecation), pelvic floor dyssynergia, pudendal neuralgia, and hemorrhoids.

Devices according to embodiments of the present invention can adopt a variety of configurations that include a generally rod-like body portion having two ends, with at least one of the ends having a bulbous tip. Either end of the devices may be used for therapies according to the present invention, as needs dictate, to provide targeted pressure and/or temperature therapy. The devices according to the present invention are thus capable of producing a localized or targeted constant pressure to internal treatment points during a treatment session while providing targeted heat (cryogenic or thermal, as desired or appropriate) therapy.

The body portions for such targeted treatment devices can be either straight or bent to facilitate positioning and manipulation of the tip of the inserted end of the device during use. Preferably, the devices are formed integrally having a generally cylindrical rod-like shape and circular cross-section shape. The bulbous tip preferably comprises a smooth semi-sphere shape formed on at least one end of the body portion. The semi-spherical shaped tip has a diameter slightly larger then the body portion of the device.

In most preferred embodiments of the invention, the body portion of the targeted treatment device has two bends that cause the device to take on a general shape similar to an elongated "S" or lightning bolt configuration. Such S-shaped configuration makes it easier for patients to hold the device while achieving various angles of entry and directions of pressure to self-administer therapy without assistance of another person.

Other most preferred embodiments of the present invention are particularly suitable for delivering cold/warm therapy internally to treatment sites within the vagina and rectum in addition to pressure therapy. Targeted treatment devices according to embodiments of the invention are constructed of medically accepted materials that are both sufficiently strong so as to be safe for applying significant pressure, easy to clean and disinfect/sterilize, and able to easily be heated or chilled to a treatment temperature and retain and transmit that heat or cold to tissue during therapy. In most preferred embodiments of the invention, the treatment devices are formed of one integral piece of medical grade glass, such as Type 1 borosilicate or equivalent medical glass. Alternative but less preferred materials include stainless steel, silicone, and other analogous materials.

A method according to an aspect of the present invention is directed to the relief of pelvic region symptoms relating to diseases, disorders, syndromes and conditions of the pelvic region by targeted internal therapy. The method includes locating one or more intra-rectal or intra-vaginal treatment points within the vaginal or rectal cavity of a human subject, with the treatment points being locations of muscle spasms, trigger points or sites of symptoms. A handheld device is provided that includes a body portion having two ends, including a first end that terminates in a generally bulbous tip. The handheld device is integrally formed from a nonporous material capable of holding temperature and transmitting heat or cold energy to tissue. The device is treated to raise or lower the temperature of the device, and then an end of the device is inserted into the subject's rectal or vaginal cavity. The inserted end is thereby brought into contact with one of the treatment points, and contact is maintained with the treatment point to cause a therapeutic response to occur.

Additionally, a method according to another aspect of the present invention is directed to the relief of pelvic region symptoms relating to interstitial cystitis by targeted internal therapy. The method includes locating one or more intra-rectal or intra-vaginal treatment points within the vaginal or rectal cavity of a human subject, with the treatment points being locations of muscle spasms, trigger points and sites of symptoms. A handheld device is provided that includes a body portion having two ends, with a first one of the ends terminating in a generally bulbous tip. The handheld device is integrally formed from a nonporous material capable of holding temperature and transmitting heat or cold energy to tissue. The device is treated to raise or lower the temperature of the device, and then one of the ends of the device is inserted into the subject's rectal or vaginal cavity. The inserted end is thereby brought into contact with one of the treatment points, and contact is maintained with the treatment point to cause a therapeutic response to occur.

Further, a method according to yet another aspect of the present invention is directed to the relief of pelvic region symptoms of pain or discomfort by targeted internal pressure and temperature therapy. The method includes locating one or more intra-rectal or intra-vaginal treatment points within the vaginal or rectal cavity of a human subject, with the treatment points being locations of muscle spasms, trigger points and sites of symptoms. A handheld device is provided that includes a body portion having two ends, including a first end that terminates in a generally spherical bulbous tip. The handheld device is integrally formed from a nonporous medical grade glass material capable of holding temperature and transmitting heat or cold energy to tissue. The device is treated to raise or lower the temperature of the device, and then an end of the device is inserted into the subject's rectal or vaginal cavity. The inserted end is thereby brought into contact with one of the treatment points and pressure is applied via the handheld device. Contact is maintained with the treatment point to cause a therapeutic response to occur.

The various embodiments of the invention having thus been generally described, several illustrative embodiments will hereafter be discussed with particular reference to several attached drawings.

DETAILED DESCRIPTION OF THE PREFERRED EMBODIMENTS

Figure 1A:
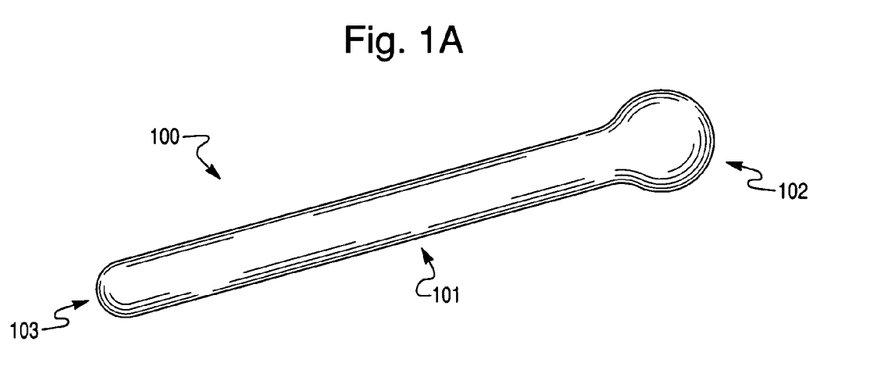
FIG. 1A is a side view drawing depicting a device according to a first embodiment of the present invention.
Figure 1B:
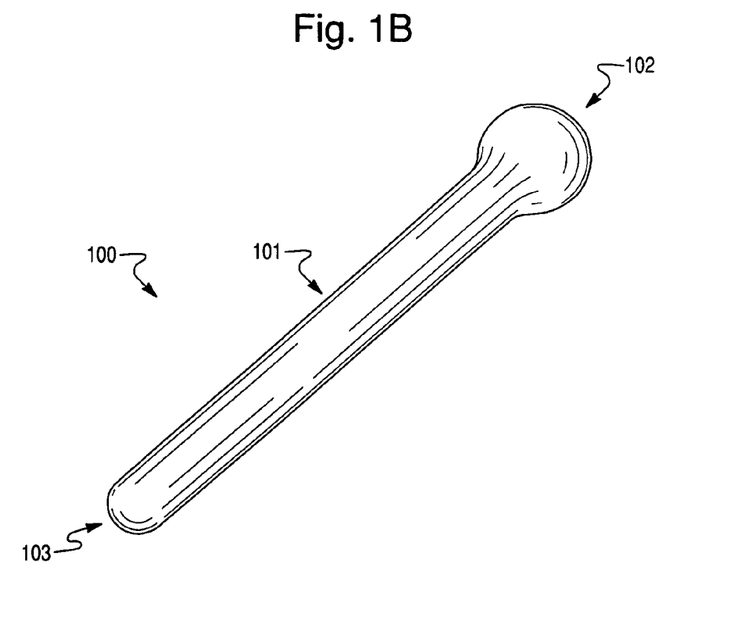
FIG. 1B is a perspective view drawing depicting the device according to the first embodiment of the present invention.

Referring first to FIG. 1A and FIG. 1B, there is depicted a targeted therapy device 100 according to a first embodiment of the present invention. As shown in the drawings, the device 100 has a generally cylindrical rod-like shape, wherein it has a generally round shape in cross-section. The device has a body portion 101 and a first end 102 attached to the body portion, which first end 102 terminates in a bulbous and rounded tip. Preferably, the tip at the first end is a smooth semi-sphere shape, as depicted. The second end 103 of the device 100 preferably terminates in a rounded tip as depicted.

The shape of device 100 as depicted in the drawings is particularly advantageous for uses according to the methods of the present invention for various reasons. First, the semi-spherical shaped tip at the first end 102 has a diameter slightly larger then the body portion 101 that forms a majority of the device 100. This relationship of first end tip diameter and body portion diameter serves several functions. First, the bulbous tip can be utilized as a handle when the second end 103 of the device is used for treatment. Second, the first end 102, meaning the bulbous tip itself, alternatively can be inserted for treatment, thus providing two unique diameters and tip shapes on a single device for treatment. Understandably, the smaller of the two ends can be used for certain treatments (or even initial dilation), while the larger of the two ends for others, as each will provide different pressure and temperature transfer characteristics.

In any event, the tip of the first end 102 or second end 103 can be located by the patient or physical therapist such that it touches the appropriate treatment site (such as a myofascial trigger point or area of pain). Also, if desired, lateral pressure can be used on the body portion 101 to transfer that pressure predominantly to the treatment site.

Figure 2A:
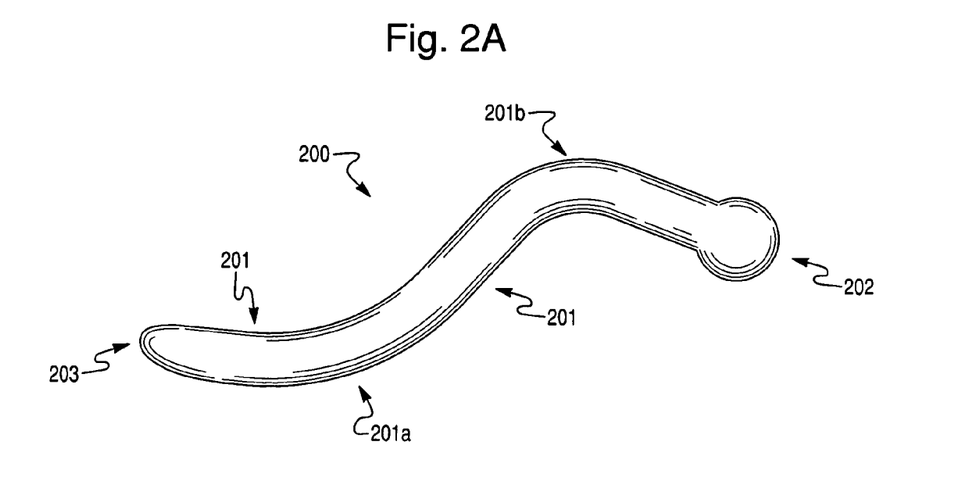
FIG. 2A is a side view drawing depicting a device according to a first embodiment of the present invention.
Figure 2B:
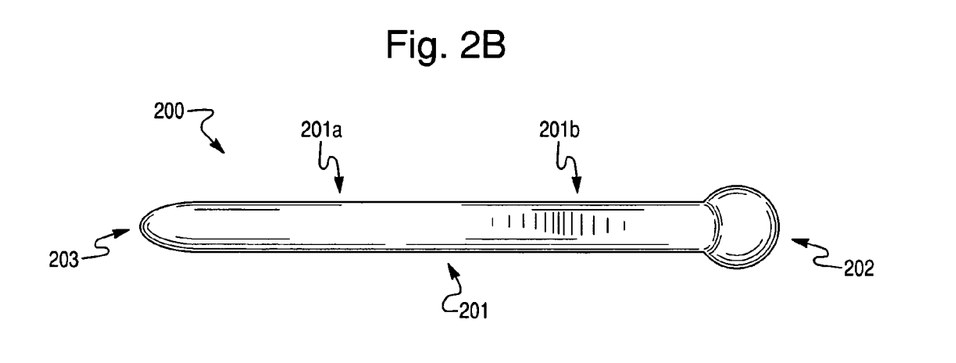
FIG. 2B is a top view drawing depicting the device according to the second embodiment of the present invention.
Figure 2C:
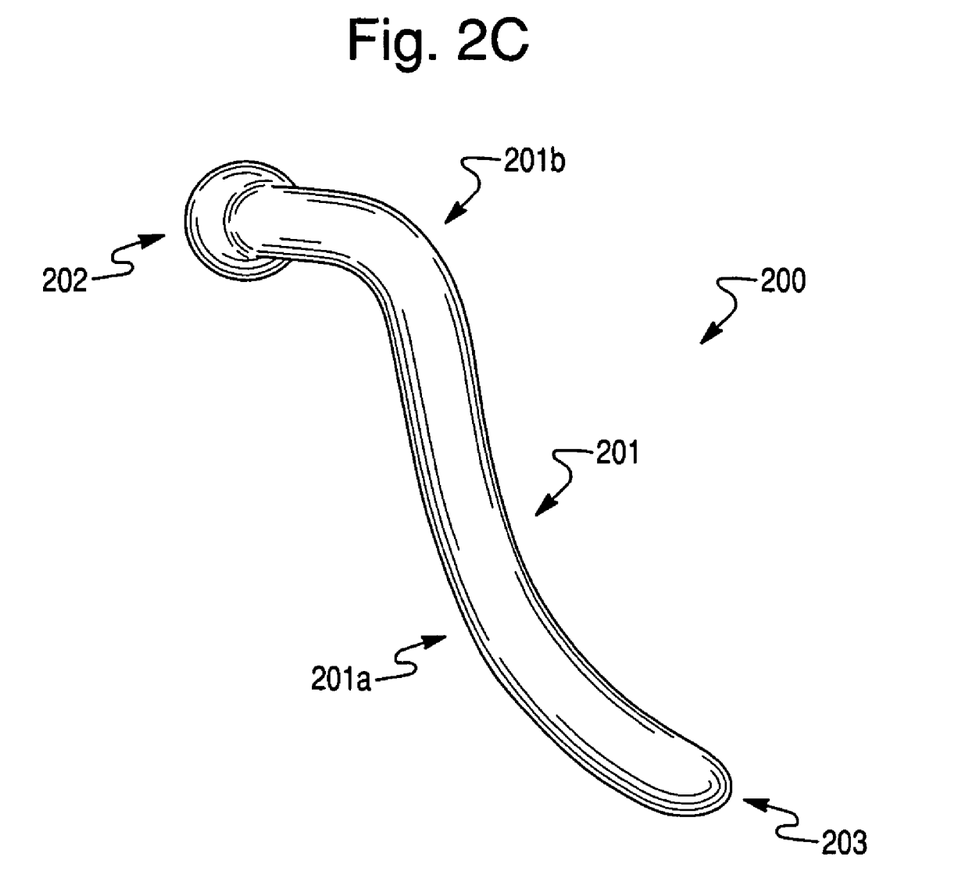
FIG. 2C is a perspective view drawing depicting the device according to the second embodiment of the present invention.

Referring now to FIG. 2A, FIG. 2B, and FIG. 2C, there is depicted a second embodiment of a targeted therapy device 200. As shown in the drawings, the device 200 has a body portion 201 that is formed from a generally cylindrical rod-like shape that has two bends 201a and 201b that cause the device 200 to take on a shape similar to an "S" or lightning bolt configuration. The body portion 201 of the device is divided into three sections by the bends 201a and 201b, and has a first end 202 formed on the section terminating the body portion at the end nearest bend 201b and a second end 203 formed on the section terminating the body portion at the end nearest bend 201a. The first end 202, similar to device 100, terminates in a bulbous and rounded tip, preferably with the tip taking a smooth semi-sphere shape as depicted. Similarly, the second end 203 of the device 200 terminates in a rounded tip. The entire device 200 generally has round cross section shapes.

The shape of device 200 as depicted in the drawings is particularly advantageous for certain uses according to the methods of the present invention for various ergonomic reasons. Like with device 100, the semi-spherical shaped tip at the first end 202 has a diameter slightly larger then the body portion 201, providing similar advantages for treatment options and handling characteristics. Bends 201a and 201b differentiate device 200 from device 100, however, for ease of self-use by certain patients in at-home settings. Understandably, the S-shaped configuration obtained will make it easier for patients to hold the device 200 while achieving various angles of entry and directions of pressure to self administer therapy without assistance of another person.

Typically, a device 100 as depicted in FIG. 1A and FIG. 1B will have, for typical uses in adults, a semi-spherical tip that measures approximately 27.5 millimeters while the diameter of the body portion 101 is approximately 16 millimeters. A suitable device 100 length from second end 103 to first end 102 would be approximately 156 millimeters. This shaft length is preferred as, for average adult females, it is sufficiently short to limit the chances of possible injury to the cervix through misuse or accident. The diameter of the body portion 101 allows the user easier insertion into the sensitive tissue of the vagina and/or rectum for pressure and temperature therapy. For example, the second end 103 can be inserted first to relax muscles before the larger diameter first end 102 is inserted. These dimensions and relative sizes, of course, can vary while retaining the general qualities of the device 100.

The device 200 as depicted in FIG. 2A, FIG. 2B and FIG. 2C will have, for typical uses in adults, a semi-spherical tip that measures approximately 27.5 millimeters while the diameter of the body portion 101 is approximately 16 millimeters (these dimensions being substantially the same as the corresponding dimensions for device 100). A suitable device 200 length from second end 203 to first end 202 (measured "as the crow flies" from tip to tip without following the curves of the body portion 201) would be approximately 185 millimeters. The angle for the bend 201b is approximately 100 to 110 degrees while the angle for the bend 201a can be approximately the same, but preferably with a more gradual bend (e.g., such as occurring over approximately 60 to 70 millimeters of the body portion 201 length). The shaft length, diameters and shape of this preferred embodiment of the present invention is advantageous because it allows the user to comfortably self-administer heat/cold therapy and/or apply pressure to trigger or tender points in the vagina or rectum, which would otherwise be a difficult, if not impossible, task without the help of a therapist or partner.

One skilled in the art will appreciate that the exact shape and dimensions of the particular devices 100 and 200 depicted are not essential to practice of the present invention. However, the designs depicted are particularly useful and preferred because the smooth design does not irritate or damage delicate tissues that line the vaginal or rectal cavities during use and has no sharp or pointy edges or projections that could invite injury. Further, this design is particularly preferable for casting of the devices from the most desired materials. However, it should be appreciated that these designs can be insubstantially altered, such as by, for example, changing the cross-section shape of various portions (the handle or either end) of the devices to oval shapes or by providing double bulbous tips with one on each end of the device (and having, for example, different diameters).

In all embodiments of the invention, it is necessary that the material of construction for the devices be one that is strong so as to be safe for applying significant pressure, easy to clean and disinfect/sterilize, and able to easily be heated or chilled and retain and transmit that heat or cold during therapy. Further, it is preferred that the devices be constructed of one integral piece of material to promote strength of the device and to prevent seams or edges from forming which can cause injury or hamper cleaning and disinfection/sterilization. Thus, in most preferred embodiments of the invention, the devices are formed of one integral piece of medical grade glass. In particular, "Type 1 borosilicate" or equivalent medical glass is preferred as it is non-porous, hypoallergenic, 100% lead-free, forms smooth surfaces to the touch, is strong, and holds and transmits heat and cold very well. Safety of the devices formed from such glass can be readily tested for safety after manufacture and before use, such as by polariscope to ensure integrity of the glass. Such medical grade glass has a proven history of durability in the medical and scientific fields and is thereby readily accepted by doctors, physical therapists and other health care providers. Further, Type 1 borosilicate glass being non-porous not only makes the devices slick and comfortable during use, but also makes them easy to clean and disinfect/sterilize, and prevents them from absorbing odors or germs readily (assuming proper cleaning before and/or after each use). Thus, medical grade glass provides a significantly decreased risk of infections in women or men, relative to latex, rubber, plastic or acrylic. In addition, medical grade glass is dishwasher, refrigerator and microwave oven safe, making devices made entirely from this material easier to clean and disinfect than devices made from other materials.

Alternative but less preferred materials include stainless steel, silicone, and other analogous materials for the formation of the devices of the present inventions. Additionally, these alternative materials may or may not be constructed with a frozen gel pack or similar warming or cooling component to be inserted into the product to prolong the warm or cool state.

Medical grade class is also preferred because it is highly capable of holding and transmitting heat or cold to tissue of a person while being capable of maintaining strength and integrity at very high and low temperatures. However, for normal purposes, during use the devices may be chilled to temperatures of approximately 45 degrees Fahrenheit and above for cryogenic therapy or heated to approximately 105 degrees Fahrenheit or below for thermal therapy. As in any type of temperature therapy, overuse of hot and cold therapy is not desirable. Medical grade glass, however, has the added benefit in that they return to body temperature within 8 to 10 minutes if heated or chilled within the above parameters, thus naturally limiting therapy duration to common clinically suggested timeframes for temperature therapy. Devices that use electrical or chemical means to create temperature gradients in the devices do not have this built-in treating duration-limiting mechanism.

It should be apparent to one skilled in the art that devices according to the present invention can take on various shapes and dimensions, such as, for example, depicted in the drawings with the straight embodiment and bent embodiment of the present invention, or combinations thereof. Use of alternative materials and product sizes are available to produce a unique product that is made for the same uses as that of straight embodiments of the present invention and bent embodiments of the present invention.

Direct stimulation of the pelvic floor nerves using devices and method according to the present invention advantageously bypasses other unrelated nerve groups at the sacral roots. Nerves in this region that may be targeted for stimulation include the pudendal nerve, pelvic nerve, and the clitoral branches of the pudendal nerve. The pudendal nerve and its branches are somatic nerves that originate from the sacral nerve roots. These and other somatic nerves emanating from the sacral nerve roots are preferably stimulated to treat dysfunctions of perineal structures, such as urinary and/or bowel incontinence, urgency, frequency, and/or pain. For instance, stimulation of the urethral branch of the pudendal nerve may be used to inhibit defecation, thereby treating fecal incontinence. Additionally or alternatively, stimulation of the inferior rectal branch of the pudendal nerve, which innervates the external anal sphincter, may also inhibit defecation, thereby treating fecal incontinence. Stimulation of other somatic nerves innervating the rectum and/or colon may treat constipation, fecal retention, and/or colorectal hypomotility. Stimulation of one or more other pudendal nerve branches (e.g., the dorsal nerve of the clitoris/penis) may be used as a treatment of, e.g., urinary urge incontinence and/or detrusor hyperreflexia. Stimulation of nerves innervating the urethra and/or detrusor muscle may treat urinary retention, while stimulation of nerves innervating the internal and/or external urethral sphincter or their intramuscular branches may treat urinary stress incontinence. Stimulation of nerve(s) innervating the clitoris and/or vagina may treat vaginismus, dyspareunia, anorgasmia, or other female sexual dysfunction.

The preferred method of using the devices described herein generally starts with identifying and locating one or more intra-anal or intra-vaginal treatment points selected from the group consisting of locations of intra oral muscle spasms, trigger points, nerve clusters, and other points of pelvic floor dysfunction internally within the vaginal or rectal cavity of a human subject. The device according to the present invention is then chilled or heated to the desired treatment temperature. Optionally, of course, the device could first be used at room temperature for initial insertion and stretching of the anal or vaginal opening and then chilled or heated to the desired treatment temperature.

The particular end of the device chosen for the particular treatment is then inserted into the anal or vaginal cavity of the patient (using lubrication as necessary), and the tip of that end is brought into contact with one of the treatment points. The end of the device is held in contact with the treatment point (optionally applying mild to firm pressure) until the desired relief response is obtained, such as a trigger point release, pain relief, discomfort relief, inflammation abating, etc. Therapy can then continue to additional treatment points.

Optionally, manual pressure is applied to the extent that the user can tolerate, sometimes relaxing and then periodically reapplying the pressure to cause a particular trigger point to release or to cause sensations of pain or discomfort to abate and thereby eliminate or minimize the pelvic area symptom that was previously experienced by the patient. Similarly, hot and cold therapy can be used in alternating fashion.

For example, to locate treatment points, such as muscle tissue where trigger points are found, a patient or physical therapist can use the device in a trial and error manner, moving the inserted end internally to locate areas of pain or trigger points. The device is shifted upwardly, downwardly or sidewise and manual pressure can be applied to find tender or trigger points or other areas of localized pain, discomfort, or undesired symptoms. Similarly, treatment points can be selected by physicians or physical therapists based upon general diagnoses (such as instructing male patients to apply cold therapy targeted near the front wall of the rectum when cases of non-bacterial prostatitis are diagnosed).

As will be readily appreciated by one skilled in the art, an advantage of the invention is its portability and that the patient can utilize this invention whenever tissue pain or other symptoms arise. The devices according to the invention are easily heated or cooled by a variety of means commonly available both in the home and while traveling, including hot or cold water, ice, refrigerators, and microwave ovens. No longer is the patient's treatment schedule dependent on the time slot available to him or her in the physical therapist's office to alleviate the pain.

Therefore, as described above, straight embodiments of the present invention or bent embodiments of the present invention both provide all the benefits of cold/warm therapy to help relieve pain and relax muscles in the vagina and rectum to resolve various symptoms, including pain, inflammation, swelling, burning and stress/tension. They can be reused again and again, unlike chemical hot or cold packs, and with little expense.

Particular examples of suitable uses of the devices of the present invention according to the methods herein disclosed include the following. For chronic tightness of the pelvic floor, but not an acute exacerbation, warmed devices of the present invention can be inserted for 5 to 10 minutes at a time 2-3 times per day. For an acute flare-up of tightness of the pelvic floor of a normally "under control" condition, chilled devices of the present invention can be inserted for 5 to 10 minutes 2-3 times per day. Additionally, for pain during or after intercourse, devices according to the present invention may be inserted warm prior to intercourse for 5 minutes to relax pelvic floor muscles. Then, after intercourse, a device can be inserted cold for 5-10 minutes (two devices may be needed). The cold treatment can be repeated an hour or two later if necessary.

Similarly, for treatment of chronic low level pelvic pain, devices can be used warm for 5 minutes to relax pelvic floor muscles and 3 minutes cold to reduce inflammation—alternating 3 to 5 times and ending with a cold session. This can be repeated once or twice daily. (Again, two devices may be needed). For episodes of severe pain, the device can be in either the warm or cold state (whichever works best for the patient) not to exceed 10 minutes per hour.

For release of tight trigger point muscles in the vagina or rectum, the device can be used warmed to simultaneously apply gentle pressure to each trigger point for 30-90 seconds. If the trigger point does not immediately release, the warming therapy could be delivered (without applying significant pressure), and then pressure therapy later retried.

With these generalized potential situations for using various embodiments of the invention being thus described, several examples will now be provided to support the benefits of the present invention.

Example 1

A physical therapist reported being referred from a doctor a patient with a diagnosis of levator ani syndrome (chronic tension of the levator muscle, sometimes stress derived) and associated constipation. The patient was an age 74 woman that reported having symptoms of severe pain in her rectum and vagina after a bowel movement on a daily basis, which symptoms had been present for 6 years. Treatment with various medications had been tried over that time period without resulting in relief. She sought medical care from a gastrointestinal physician and was referred to physical therapy for the treatment of her pelvic floor dysfunction.

On initial assessment patient reported her pain averaged an "8" on the common 10-point pain scale, and that she was having extreme difficulty initiating a bowel movement. On objective examination, the patient was noted to have severe muscle guarding in her puborectalis, pubovaginalis and iliococcygeus musculature bilaterally. The patient was instructed in manual myofascial stretching techniques and was recommended to use a device according to embodiments of the invention (in particular, a bent embodiment similar to device 200 described above) for self-administration of trigger point release within the vagina and rectum. The patient was able to administer targeted treatment independently with the device vaginally, and found it gave her good relief of her pain symptoms. Patient also reported placing the device (made of borosilicate glass) in the refrigerator to utilize cryotherapy in addition to the manual pressure techniques and found that this helped the most with relieving her pain symptoms.

After 4 weeks of using the device according to the prescribed method with cryotherapy, the patient was able to independently self-manage her pain symptoms. Her average pain had decreased to 1-2 on the 10 point scale, and she reported no longer was having difficulty initiating a bowel movement. The patient also reported that the device was easy to use and very effective in reducing her pain complaints.

Example 2

A female patient, age 48, suffered from interstitial cystitis for a period of years. Following other unsuccessful treatments, the patient was referred to a physical therapist to obtain vaginal trigger point release treatments for pelvic floor dysfunction. The patient reported that internal trigger point release was helpful, but that severe pain would be experienced after and between treatment sessions.

The therapist then suggested that the patient try targeted pressure and cryogenic therapy using a treatment device according to the embodiments of FIG. 1a-1c to alleviate pain following and between therapy sessions. The patient reported significant pain relief using the device vaginally 5-10 minutes as needed after first chilling the device in a refrigerator.

Example 3

An adult female patient presented with chronic pain in the pelvic region associated with her diagnosed disease Interstitial Cystitis. She had the disease for approximately 8 years and had tried but not experienced success with various medications to manage her pain symptoms. Patient was instructed in the use of a targeted pressure and temperature treatment device according to the embodiments of the invention and utilized the device for both thermal and cryogenic therapy vaginally. The patient reported benefits from using the device either heated or cold with a preference for cold. The patient reported that her then current pain symptoms were lessened following each use by at least 3 points on a pain scale of 1 to 10.

Example 4

An age 38 male patient suffering from pelvic floor dysfunction due to symptoms associated with chronic pelvic pain syndrome reported pain and spasms associated with ejaculation. In conjunction with the advice of a physical therapist, the patient began to use embodiments of devices of the present invention to perform temperature therapy prior to intercourse. In particular, the patient used a device warmed above body temperature prior to intercourse in conjunction with his normal physical therapy routine to help relax his pelvic floor muscles. The patient reported significant improvement in symptoms.

Example 5

An adult woman diagnosed with vulvodynia, vulvar vestibulitis, and trigger and tender points began using devices according to the present invention upon the recommendation of her gynecologist and physical therapist. The patient reported having struggled with pain and irritation associated with these diagnosed conditions for a period of over 7 years.

The patient was instructed by the gynecologist to perform cryogenic therapy according to embodiments of the present invention to alleviate symptoms of pain and irritation due to vulvar vestibulitis. In conjunction with the physical therapist, the patient also began to perform self-administered thermal therapy according to embodiments of the invention prior to physical therapy sessions to help relax her pelvic floor muscles, and also used devices according to the present invention to self-administer trigger point release pressure therapy at home.

The patient reported that the cryogenic therapy alleviated her pain significantly and that the thermal and pressure therapy helped her relax her pelvic floor muscles prior to intercourse and during trigger point pressure therapy.

Having described preferred embodiments of the invention it will now become apparent to those of ordinary skill in the art that other embodiments incorporating these concepts may be used. Accordingly, it is submitted that the invention should not be limited to the described embodiments but rather should be limited only by the spirit and scope of the appended claims. Although the invention has been described and illustrated with a certain degree of particularity, it is understood that the present disclosure has been made only by way of example, and that numerous changes in the combination and arrangement of steps or orientation of parts can be resorted to by those skilled in the art without departing from the spirit and scope of the invention, as hereinafter claimed.

I claim:

1. A method for the relief of pelvic region symptoms relating to diseases, disorders, syndromes and conditions of the pelvic region by targeted internal therapy, said method comprising the steps of:
   locating one or more intra-rectal or intra-vaginal treatment points within the vaginal or rectal cavity of a human subject, said treatment points being selected from the group consisting of locations of muscle spasms, trigger points and sites of said symptoms;
   providing a handheld device comprising a body portion having two ends, said handheld device being integrally formed from a nonporous material capable of holding temperature and transmitting heat or cold energy to tissue, a first end of said device ends terminating in a generally bulbous tip;
   treating said device to raise or lower the temperature of the device;
   inserting one of said device ends into the subject's rectal or vaginal cavity and thereby bringing the inserted end into contact with one of the treatment points;
   maintaining contact with the treatment point to cause a therapeutic response to occur; and
   applying pressure to said treatment point in contact with said inserted end, wherein the applying pressure step is performed for approximately 30 seconds to approximately 90 seconds.

2. The method according to claim 1, wherein said generally bulbous tip has a diameter greater than a diameter of said body portion.

3. The method according to claim 2, wherein said generally bulbous tip comprises a semi-sphere.

4. The method according to claim 1, wherein said therapeutic response includes a trigger point release response, a pain relief occurs, a discomfort relief response, or an inflammation abating response.

5. The method according to claim 1, wherein the relief response comprises softening of the treatment point.

6. The method according to claim 1, further comprising:
   repositioning the handheld device;
   bringing the inserted end into contact with another of the treatment points; and
   repeating said maintaining contact with the treatment point step.

7. The method according to claim 1, wherein said device is used internally for approximately 8-10 minutes.

8. The method according to claim 1, wherein said device is used internally until it returns to room or body temperature.

9. The method according to claim 1, wherein said treating of said device comprises heating the device to a temperature above body temperature and below approximately 105° F.

10. The method according to claim 1, wherein said treating of said device comprises heating the device to a temperature below room temperature and above approximately 45° F.

11. The method according to claim 1, wherein the bulbous tip of the handheld device has a diameter that is approximately 1.5 to 2 times the diameter of said body portion.

12. The method according to claim 11, wherein the bulbous tip of the handheld device has a diameter of approximately 27.5 mm.

13. The method according to claim 1, wherein the handheld device is integrally formed from medical grade glass.

14. The method according to claim 13, wherein said medical grade glass is Type 1 borosilicate.

15. The method according to claim 1, wherein said symptoms are selected from the group consisting of pain, discomfort, soreness, weakness, inflammation, pressure, muscle spasms, itching, burning and irritation.

16. A method for the relief of pelvic region symptoms relating to diseases, disorders, syndromes and conditions of the pelvic region by targeted internal therapy, said method comprising the steps of:

locating one or more intra-rectal or intra-vaginal treatment points within the vaginal or rectal cavity of a human subject, said treatment points being selected from the group consisting of locations of muscle spasms, trigger points and sites of said symptoms;

providing a handheld device comprising a body portion having two ends, said handheld device being integrally formed from a nonporous material capable of holding temperature and transmitting heat or cold energy to tissue, a first end of said device ends terminating in a generally bulbous tip;

treating said device to raise or lower the temperature of the device;

inserting one of said device ends into the subject's rectal or vaginal cavity and thereby bringing the inserted end into contact with one of the treatment points;

maintaining contact with the treatment point to cause a therapeutic response to occur;

and applying pressure to said treatment point in contact with said inserted end, wherein said applying of pressure comprises delivering pressure at said treatment site at or below a moderate discomfort level for the patient, wherein said moderate discomfort level is defined as below a point at which the patient winces or tenses involuntarily.

17. A method for the relief of pelvic region symptoms relating to diseases, disorders, syndromes and conditions of the pelvic region by targeted internal therapy, said method comprising the steps of:

locating one or more intra-rectal or intra-vaginal treatment points within the vaginal or rectal cavity of a human subject, said treatment points being selected from the group consisting of locations of muscle spasms, trigger points and sites of said symptoms;

providing a handheld device comprising a body portion having two ends, said handheld device being integrally formed from a nonporous material capable of holding temperature and transmitting heat or cold energy to tissue, a first end of said device ends terminating in a generally bulbous tip;

treating said device to raise or lower the temperature of the device;

inserting one of said device ends into the subject's rectal or vaginal cavity and thereby bringing the inserted end into contact with one of the treatment points;

maintaining contact with the treatment point to cause a therapeutic response to occur; and applying pressure to said treatment point in contact with said inserted end, wherein the applying pressure step comprises applying pressure at a plurality of dissimilar angles to the treatment point.

18. A method for the relief of pelvic region symptoms relating to diseases, disorders, syndromes and conditions of the pelvic region by targeted internal therapy, said method comprising the steps of:

locating one or more intra-rectal or intra-vaginal treatment points within the vaginal or rectal cavity of a human subject, said treatment points being selected from the group consisting of locations of muscle spasms, trigger points and sites of said symptoms;

providing a handheld device comprising a body portion having two ends, said handheld device being integrally formed from a nonporous material capable of holding temperature and transmitting heat or cold energy to tissue, a first end of said device ends terminating in a generally bulbous tip;

treating said device to raise or lower the temperature of the device;

inserting one of said device ends into the subject's rectal or vaginal cavity and thereby bringing the inserted end into contact with one of the treatment points;

and maintaining contact with the treatment point to cause a therapeutic response to occur; and wherein the body portion of the handheld device has at least two bends such that said device adopts an S-shaped or lightning bolt shape in profile.

19. A method for the relief of pelvic region symptoms relating to diseases, disorders, syndromes and conditions of the pelvic region by targeted internal therapy, said method comprising the steps of:

locating one or more intra-rectal or intra-vaginal treatment points within the vaginal or rectal cavity of a human subject, said treatment points being selected from the group consisting of locations of muscle spasms, trigger points and sites of said symptoms;

providing a handheld device comprising a body portion having two ends, said handheld device being integrally formed from a nonporous material capable of holding temperature and transmitting heat or cold energy to tissue, a first end of said device ends terminating in a generally bulbous tip;

treating said device to raise or lower the temperature of the device;

inserting one of said device ends into the subject's rectal or vaginal cavity and thereby bringing the inserted end into contact with one of the treatment points;

and maintaining contact with the treatment point to cause a therapeutic response to occur; and wherein said patient has been diagnosed with an inflammatory, non-infectious pain syndrome selected from the group consisting of pelvic floor dysfunction, dyspareunia, vaginismus, non-bacterial prostatitis, vulvodynia and interstitial cystitis.

20. The method according to claim 19, wherein the handheld device is integrally formed from medical grade glass.

21. The method according to claim 20, wherein said medical grade glass is Type 1 borosilicate.

22. The method according to claim 19, wherein said generally bulbous tip has a diameter greater than a diameter of said body portion.

23. The method according to claim 22, wherein said generally bulbous tip comprises a semi-sphere.

24. A method for the relief of pelvic region symptoms relating to interstitial cystitis by targeted internal therapy, said method comprising the steps of:
   locating one or more intra-rectal or intra-vaginal treatment points within the vaginal or rectal cavity of a human subject, said treatment points being selected from the group consisting of locations of muscle spasms, trigger points and sites of said symptoms;
   providing a handheld device comprising a body portion having two ends, said handheld device being integrally formed from a nonporous material capable of holding temperature and transmitting heat or cold energy to tissue, a first end of said device ends terminating in a generally bulbous tip and the body portion of the handheld device having at least two bends such that said device adopts an S-shaped or lightning bolt shape in profile;
   treating said device to raise or lower the temperature of the device;
   inserting one of said device ends into the subjects rectal or vaginal cavity and thereby bringing the inserted end into contact with one of the treatment points;
   and maintaining contact with the treatment point to cause a therapeutic response to occur.

25. The method according to claim 24, wherein the handheld device is integrally formed from medical grade glass.

26. The method according to claim 25, wherein said medical grade glass is Type 1 borosilicate.

27. The method according to claim 24, wherein said generally bulbous tip has a diameter greater than a diameter of said body portion.

28. The method according to claim 27, wherein said generally bulbous tip comprises a semi-sphere.

29. The method according to claim 24, wherein the bulbous tip of the handheld device has a diameter that is approximately 1.5 to 2 times the diameter of said body portion.

30. The method according to claim 29, wherein the bulbous tip of the handheld device has a diameter of approximately 27.5 mm.

31. The method according to claim 24, wherein said symptoms are selected from the group consisting of pain, discomfort, soreness, weakness, inflammation, pressure, muscle spasms, itching, burning and irritation.

* * * * *

UNITED STATES PATENT AND TRADEMARK OFFICE
CERTIFICATE OF CORRECTION

PATENT NO. : 7,695,489 B2
APPLICATION NO. : 11/475996
DATED : April 13, 2010
INVENTOR(S) : Iliana Chea Brockman Page 1 of 1

It is certified that error appears in the above-identified patent and that said Letters Patent is hereby corrected as shown below:

At column 11, lines 35-36, delete "side-wise" and insert --sideways--.

At column 15, line 5, in claim 10, delete "heating" and insert --cooling--.

Signed and Sealed this
Thirtieth Day of August, 2011

David J. Kappos
*Director of the United States Patent and Trademark Office*